(12) United States Patent
Meng et al.

(10) Patent No.: US 12,029,879 B2
(45) Date of Patent: Jul. 9, 2024

(54) CONTROLLABLE PUMPING TUBING (71) Applicant: CareFusion 303, Inc., San Diego, CA (US)

(72) Inventors: Fanqing Meng, Buffalo Grove, IL (US); Siddarth K. Shevgoor, Mission Viejo, CA (US); Marc William Weimer, South Jordan, UT (US)

(73) Assignee: CAREFUSION 303, INC., San Diego, CA (US)

( * ) Notice: Subject to any disclaimer, the term of this patent is extended or adjusted under 35 U.S.C. 154(b) by 359 days.

(21) Appl. No.: 17/379,692

(22) Filed: Jul. 19, 2021

(65) Prior Publication Data

US 2022/0133994 A1   May 5, 2022

Related U.S. Application Data (60) Provisional application No. 63/110,179, filed on Nov. 5, 2020.

(51) Int. Cl.
*A61M 5/142* (2006.01)
*A61M 5/162* (2006.01)

(52) U.S. Cl.
CPC .... *A61M 5/14228* (2013.01); *A61M 5/14212* (2013.01); *A61M 5/14248* (2013.01); *A61M 5/162* (2013.01); *A61M 2205/0272* (2013.01)

(58) Field of Classification Search
CPC .............. A61M 5/162; A61M 5/14212; A61M 5/14248; A61M 2205/0272; A61M 5/14228; A61M 5/16813; A61M 2205/0238; A61M 39/28; F04B 43/082; F04B 43/1223; F04B 43/12
See application file for complete search history.

(56) References Cited

U.S. PATENT DOCUMENTS

| | | | | |
|---|---|---|---|---|
| 5,078,683 A | * | 1/1992 | Sancoff | G16H 20/17 417/474 |
| 5,964,583 A | * | 10/1999 | Danby | F04B 43/082 417/474 |
| 9,541,221 B2 | | 1/2017 | Koyama et al. | |
| 10,202,971 B2 | | 2/2019 | Kamen et al. | |
| 10,563,646 B2 | | 2/2020 | Galavotti et al. | |

(Continued)

FOREIGN PATENT DOCUMENTS

EP    0800840 A2    10/1997

OTHER PUBLICATIONS

International Search Report and Written Opinion for Application No. PCT/US2021/056294, dated Feb. 11, 2022, 14 pages.

*Primary Examiner* — James D Ponton
(74) *Attorney, Agent, or Firm* — Morgan, Lewis & Bockius LLP (57) ABSTRACT

A medical pumping system is provided. The medical pumping system includes a fluid pump having a fluid inlet connection, a fluid outlet connection, an actuator and a backing surface. A tube of an intravenous set is disposed between the fluid inlet connection and the fluid outlet connection of the fluid pump, and disposed between the actuator and the backing surface, and a binding contact interface. The tube and the actuator are coupled together by the binding contact interface. The actuator is configured to actively pull a portion of the tube into an open position during a pump cycle. A medical pump and an infusion set are also provided.

16 Claims, 6 Drawing Sheets

(56) References Cited

U.S. PATENT DOCUMENTS

| | | | |
|---|---|---|---|
| 2013/0066267 A1* | 3/2013 | Kwok | A61B 17/12136 |
| | | | 604/99.01 |
| 2013/0066273 A1* | 3/2013 | Davis | F04B 43/0072 |
| | | | 417/474 |
| 2017/0333645 A1* | 11/2017 | Alizoti | A61M 39/22 |
| 2020/0129677 A1* | 4/2020 | Payne | A61M 1/77 |
| 2020/0330683 A1 | 10/2020 | Meng et al. | |

* cited by examiner

CONTROLLABLE PUMPING TUBING

CROSS-REFERENCE TO RELATED APPLICATION(S)

This Application claims the benefit of U.S. Provisional Patent Application No. 63/110,179 entitled "CONTROLLABLE PUMPING TUBING," filed on Nov. 5, 2020, the disclosure of which is hereby incorporated by reference in its entirety for all purposes.

TECHNICAL FIELD

The present disclosure generally relates to medical fluid pumps, in particular controllable pumping tubing.

BACKGROUND

In typical medical fluid pump designs, such as infusion pumps or dialysis pumps, the pumping tubing segment and pump actuating parts, such as the plunger, upstream occluder and downstream occluder do not always contact with tubing during the filling phase. In an ideal situation, the tubing is required to immediately recover its shape after it is unloaded from the actuators. However, there is no known elastomer tubing material that has an instant tubing rebound without a time and deformation recovering delay, particularly at low temperatures under high flow rates. This slow tubing recovery leads to less fluid volume intake to the tubing segment. In order to compensate the undesirable volume to improve pump flow rate accuracy, a measurement phase has to be introduced to actually measure fluid volume in the tubing segment, followed with a cam speed justification to compensate the volume with a feedback loop mechanism. This interface between the pumping tubing segment and the pump moving parts is a passive tubing control and the flow rate accuracy almost solely relies on the elasticity of the tubing material.

For these reasons, it is desirable to provide an active tubing control that improves the fluid delivery accuracy and volume control under non-standard operating conditions, eliminate the tubing wall stickiness issue in soft polyvinyl chloride (PVC) tubing, avoid lateral friction damage on thermoplastic elastomer (TPE) tubing and eliminate the need for a feedback-loop in a measurement phase.

SUMMARY

One or more embodiments provide a medical pumping system that includes a fluid pump. The fluid pump includes a fluid inlet connection, a fluid outlet connection, an actuator and a backing surface. The medical pumping system also includes a tube of an intravenous set disposed between the fluid inlet connection and the fluid outlet connection of the fluid pump, and disposed between the actuator and the backing surface, and a binding contact interface. The tube and the actuator are coupled together by the binding contact interface. The actuator is configured to actively pull a portion of the tube into an open position during a pump cycle.

One or more embodiments provide a medical pump that includes a fluid inlet connection, a fluid outlet connection, an actuator configured to compress a portion of an intravenous tube, wherein one of the actuator is coupled to a first binding contact interface and the actuator comprises a first binding contact interface, and a backing surface opposing the actuator, wherein one of the backing surface is coupled to a second binding contact interface and the backing surface comprises a second binding contact interface. The first and second binding contact interfaces are configured to couple with first and second portions of the tube.

One or more embodiments provide an infusion set that includes a fluid inlet tube configured to couple with a fluid inlet of a fluid pump, a fluid outlet tube configured to couple with a fluid outlet of the fluid pump and a pump tube segment connecting the fluid inlet tube and the fluid outlet tube. The pump tube segment includes a first binding contact interface configured to couple with an actuator of the fluid pump, the first binding interface configured to cause tube to be actively pulled into an open position during a pump cycle, and a second binding contact interface configured to couple with a backing surface of the fluid pump, the second binding interface configured to hold the tube in place during the pump cycle.

The foregoing and other features, aspects and advantages of the disclosed embodiments will become more apparent from the following detailed description and accompanying drawings.

BRIEF DESCRIPTION OF THE DRAWINGS

The accompanying drawings, which are included to provide further understanding of the disclosure and are incorporated in and constitute a part of this specification, illustrate embodiments of the disclosure and together with the description serve to explain the principles of the disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Figure 1:
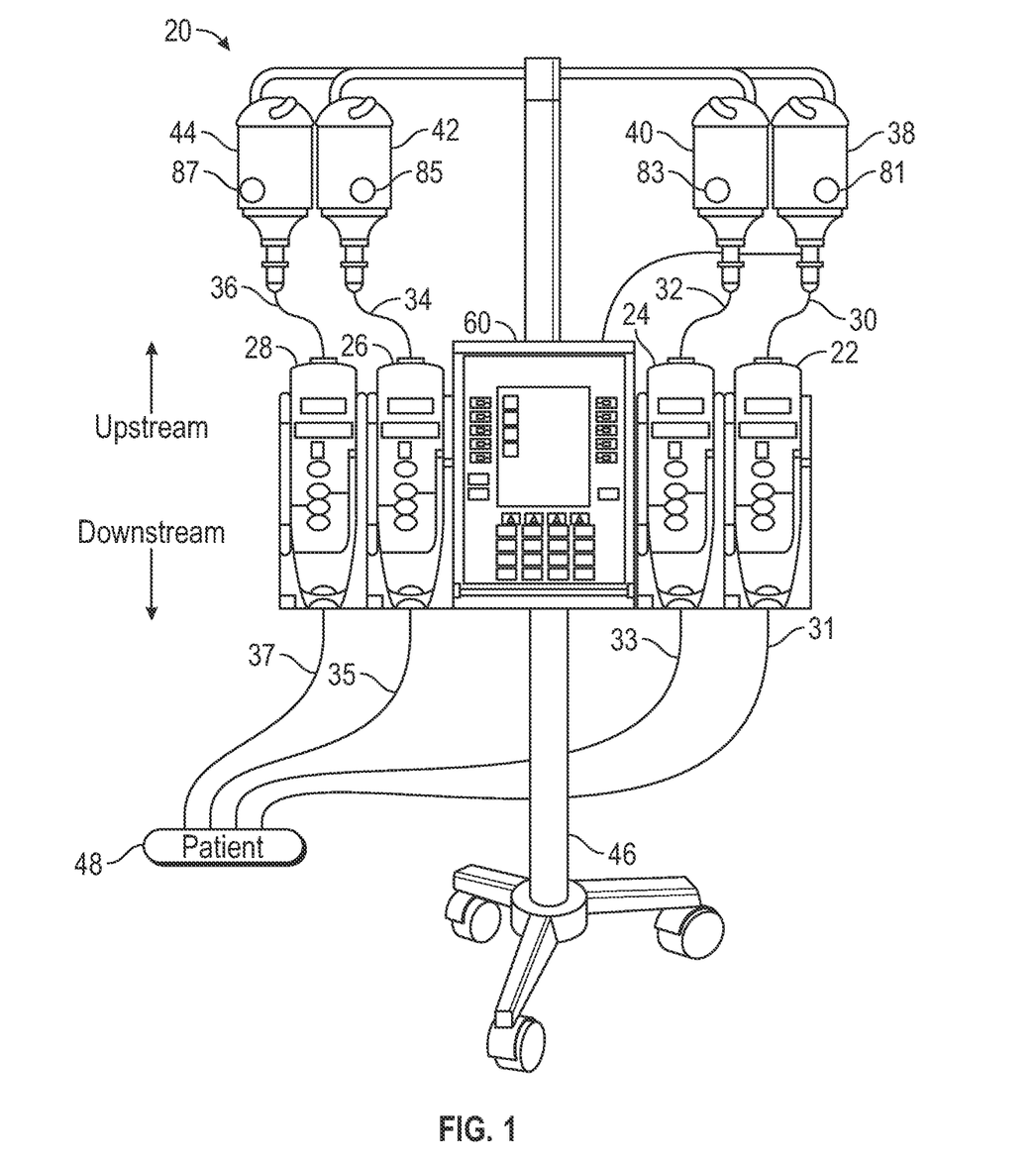
FIG. 1 depicts a perspective view of an example patient care system having four fluid infusion pumps, each of which is connected to a respective fluid supply for pumping the contents of the fluid supply to a patient, according to some aspects of the disclosure.

Referring now in more detail to the drawings in which like reference numerals refer to like or corresponding elements among the several views, there is shown in FIG. 1 a patient care system 20 having four infusion pumps 22, 24, 26, and 28 each of which is fluidly connected with an upstream fluid line 30, 32, 34, and 36, respectively. Each of the four infusion pumps 22, 24, 26, and 28 is also fluidly connected with a downstream fluid line 31, 33, 35, and 37, respectively. The fluid lines can be any type of fluid conduit, such as an IV administration set, through which fluid can flow through. It should be appreciated that any of a variety of pump mechanisms can be used including syringe pumps. It will be further understood that an infusion pump is one example of a medical fluid pump and other medical fluid pumps or pumping systems may include aspects of the active tubing control described.

Fluid supplies 38, 40, 42, and 44, which may take various forms but in this case are shown as bottles, are inverted and suspended above the pumps. Fluid supplies may also take the form of bags or other types of containers including syringes. Both the patient care system 20 and the fluid supplies 38, 40, 42, and 44 are mounted to a roller stand, IV pole 46, tabletop, etc.

A separate infusion pump 22, 24, 26, and 28 is used to infuse each of the fluids of the fluid supplies into the patient. The infusion pumps are flow control devices that will act on the respective fluid line to move the fluid from the fluid supply through the fluid line to the patient 48. Because individual pumps are used, each can be individually set to the pumping or operating parameters required for infusing the particular medical fluid from the respective fluid supply into the patient at the particular rate prescribed for that fluid by the physician. Such medical fluids may include drugs or nutrients or blood or other fluids. The infusion pumps 22, 24, 26, and 28 are controlled by a controller 60.

Fluid supplies 38, 40, 42, and 44 are each coupled to an electronic data tag 81, 83, 85, and 87, respectively, or to an electronic transmitter. Any device or component associated with the infusion system may be equipped with an electronic data tag, reader, or transmitter.

Typically, medical fluid administration sets have more parts than are shown in FIG. 1. Many have check valves, drip chambers, valves with injection ports, connectors, and other devices well known to those skilled in the art. These other devices have not been included in the drawings so as to preserve clarity of illustration.

Figure 2:
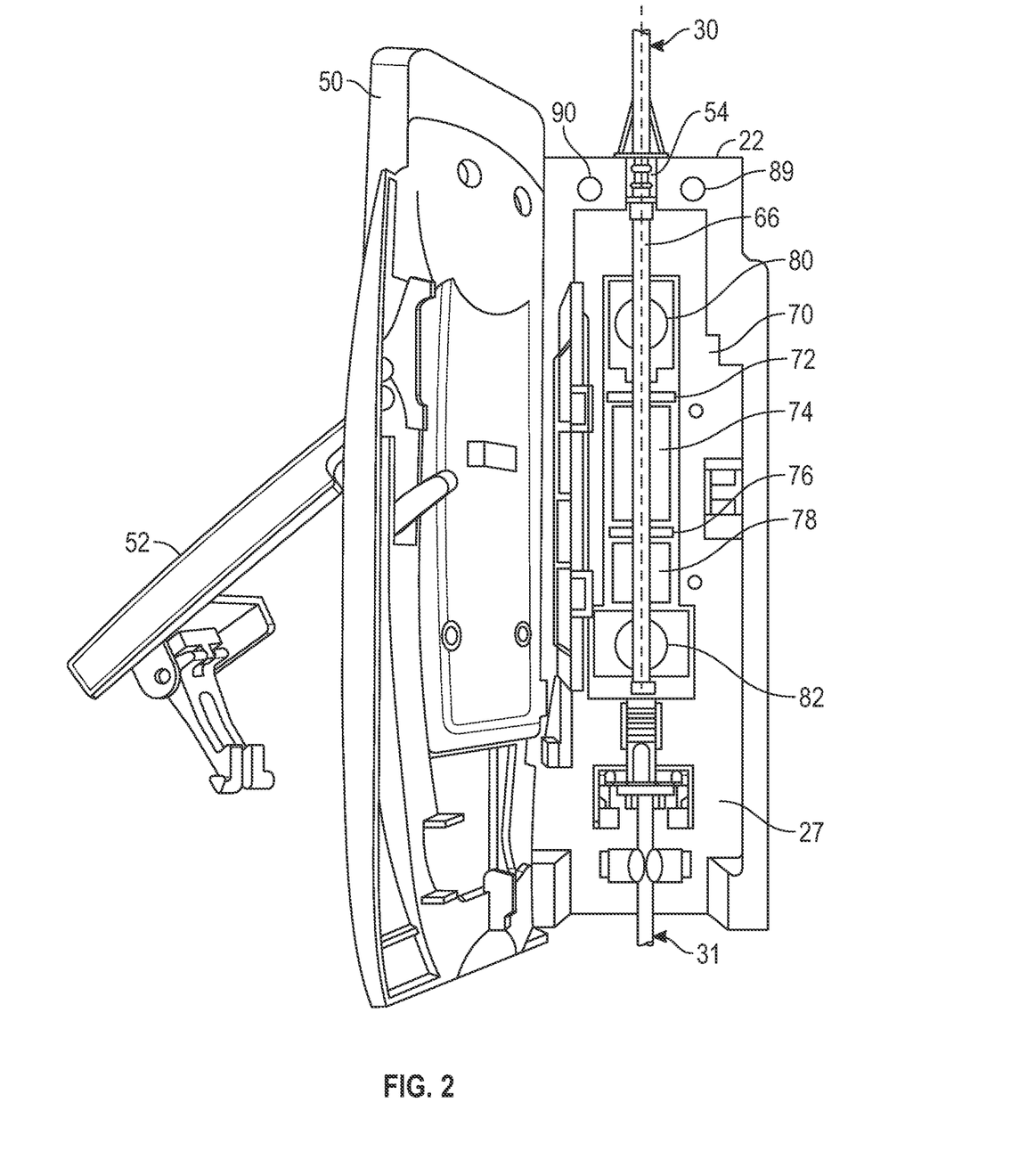
FIG. 2 depicts a perspective view of an infusion pump system, according to aspects of the disclosure.

Turning now to FIG. 2, an infusion pump 22 having a body 27 is shown in perspective view with the front door 50 open, showing the upstream fluid line 30 and downstream fluid line 31 in operative engagement with the pump 22. The infusion pump 22 directly acts on a tube 66 that connects the upstream fluid line 30 to the downstream fluid line 31 to form a continuous fluid conduit, extending from the respective fluid supply 38 (FIG. 1) to the patient 48, through which fluid is acted upon by the pump to move fluid downstream to the patient. Specifically, a pumping mechanism 70 acts as the flow control device of the pump to move fluid though the conduit. The upstream and downstream fluid lines and/or tube 66 may be coupled to a pump cassette or cartridge that is configured to be coupled to the pump 22.

The type of pumping mechanism may vary and may be for example, a multiple finger pumping mechanism. For example, the pumping mechanism may be of the "four finger" type and includes an upstream occluding finger 72, a primary pumping finger 74, a downstream occluding finger 76, and a secondary pumping finger 78. The "four finger" pumping mechanism and mechanisms used in other linear peristaltic pumps operate by sequentially pressing on a segment of the fluid conduit by means of the cam-following pumping fingers and valve fingers 72, 74, 76, and 78. The pressure is applied in sequential locations of the conduit, beginning at the upstream end of the pumping mechanism and working toward the downstream end. At least one finger is always pressing hard enough to occlude the conduit. As a practical matter, one finger does not retract from occluding the tubing until the next one in sequence has already occluded the tubing; thus at no time is there a direct fluid path from the fluid supply to the patient. The operation of peristaltic pumps including four finger pumps is well known to those skilled in the art and no further operational details are provided here.

FIG. 2 further shows a downstream pressure sensor 82 included in the pump 22 at a downstream location with respect to the pumping mechanism. The downstream pressure sensor 82 is mounted to the flow control device 70 and is located adjacent and downstream in relation to the flow control device. The downstream pressure sensor is located downstream from the flow control device, that is, at a location between the patient 48 (FIG. 1) and the flow control device, so that the connection of the correct fluid supply with the correct pump may be verified before any fluid is pumped to the patient.

With reference still to FIG. 2, an upstream pressure sensor 80 may also be included in the pump 22. The upstream pressure sensor is assigned to the flow control device or pumping mechanism 70 and, in this embodiment, is further provided as an integral part of the pump 22. It is mounted to the flow control device 70 and is located adjacent and upstream in relation to the flow control device. The upstream pressure sensor is located upstream from the flow control device, that is, at a location between the fluid supply 38 (FIG. 1) and the flow control device, so that the connection of the correct fluid supply with the correct pump may be verified before any fluid is pumped to the patient.

The pump 22 or a portion of the pump 22 may also be equipped with an electronic data tag or data transmitter. For example, as shown in FIG. 2, pump 22 may be equipped with a data tag 89 or a reader device 90 for providing or receiving infusion data. The data reader devices may include RFID readers (or receivers) or other wireless devices that are compatible with the data tags associated with the fluid containers. A data transmitter may transmit interrogation signals to the electronic data tags 81, 83, 85, 87 associated with the fluid containers for obtaining infusion data from those tags. Although referred to as data transmitting devices or RFID tags or RFID transponders, data transmitting devices may also receive or read data and may also be writable.

Typically, medical tubing is a disposable product that is used once and then discarded. The medical tubing may be formed from any suitable material, e.g., soft PVC, silicone, thermoplastic vulcanizate (TPV) (ethylene propylene diene monomer (EPDM)+polypropylene (PP)), thermoplastic polyurethane (TPU), thermoplastic styrenic elastomer (TPS) (styrene-butadiene-styrene (SBS)/styrene-ethylene-butylene-styrene (SEBS)/styrene-isoprene-rubber (SIS)/styrene-ethylene-propylene-styrene (SEPS)) and its blending with polyolefin, thermoplastic polyester elastomer (TPEE) (polyether ester) rubber). As shown in FIG. 2, medical tubing 66 may be inserted into or otherwise engaged by pump 22. Pump 22 may include any of Large Volume, patient-controlled analgesia (PCA), ambulatory pump or insulin pump that drive tubing segment(s) to deliver medication or nutrients or other medical fluids into a patient's body in controlled amounts. The medical tubing 66 is compressed when the pump door 50 is closed. With the pump door 50 closed, the medical tubing 66 is constrained within a gap 54 and directly contacted by the upstream force sensor 80. As discussed above, there are many sources of variation in measuring the force on the medical tubing 66 by the sensor 80.

Figure 3:
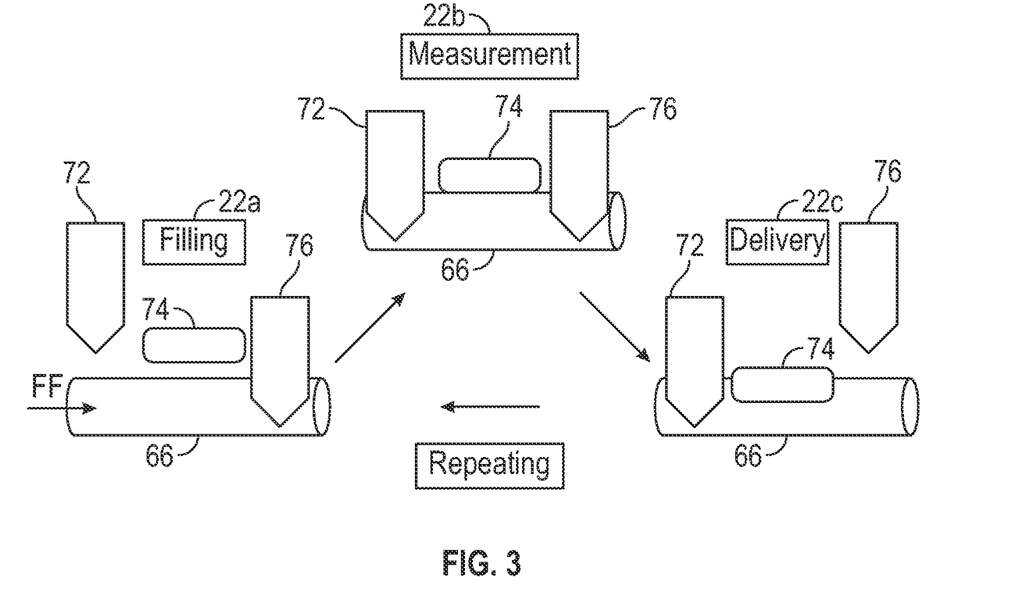
FIG. 3 depicts an illustration of a pump cycle of the infusion pump system of FIG. 2, according to aspects of the disclosure.

As shown in FIG. 3 the pump 22 has three sequential phases, including filling 22a, measurement 22b and delivery 22c. In the filling phase 22a, fluid is drawn from a fluid supply 38, 40, 42, 44 through the tubing 66 in a fluid flow FF and the upstream occluding finger 72 and the primary pumping finger 74 are disengaged from the tubing 66, while the downstream occluding finger 76 is pressed into the tubing 66. This allows fluid to flow into the tubing 66 up to the occlusion in the tubing 66 caused by the downstream occluding finger 76. In the measurement phase 22b, the upstream occluding finger 72 is pressed into the tubing 66, occluding the tubing 66 and preventing further fluid flow from the fluid supply 38, 40, 42, 44, the primary pumping finger 74 is engaged with the tubing 66 and the downstream occluding finger 76 remains pressed into the tubing 66. In the delivery phase 22c, the primary pumping finger 74 is pressed into the tubing 66 and the downstream occluding finger 76 is disengaged from the tubing 66, which causes the fluid in the tubing downstream from the upstream occluding finger 72 to flow out of the tubing 66 in a downstream direction.

During the medication delivery process 22c, when the upstream occluding finger 72 is lifted up to intentionally open the fluid path from a fully occluded position in the filling phase 22a, it is necessary that tubing 66 should perform a mechanical resilience response in order to rebound quickly and attract enough fluid volume within a sub-second time scale, particularly in the case of high flow rates up to 1200 mL/hr at low temperatures of 5 Celsius to 10 Celsius. However, commonly used tubing 66 materials such as PVC, TPE, TPU, silicone, etc. typically become rigid and deteriorate in elasticity at low temperatures, thus diminishing the resilience of the tubing 66.

In addition, the widely used tubing 66 material of PVC is known for its surface tackiness, mainly due to exuded small molecular plasticizers on the inner and outer layer surfaces of the tubing. The tackiness can be magnified at the higher end of application temperature range (5 Celsius to 40 Celsius) under flow rate as low as 0.1 mL/hr, which could adhere the inner tubing walls to each other, delaying or even preventing the opening.

From the two application scenarios described above, either the tubing 66 is unable to open enough internal diameter (ID) aperture at low temperatures under high flow rate or the opening gets delayed at high temperatures under low flow rate. Both cases can lead to under volume delivery.

In another application scenario, some tubing 66 materials, such as TPE, can lack adequate lubricity on the tubing outer layer surface. As a result, hundreds of thousands of on-off occlusion cycles may cause tubing surface damage due to abrasion from metal occluder material.

Figure 4:
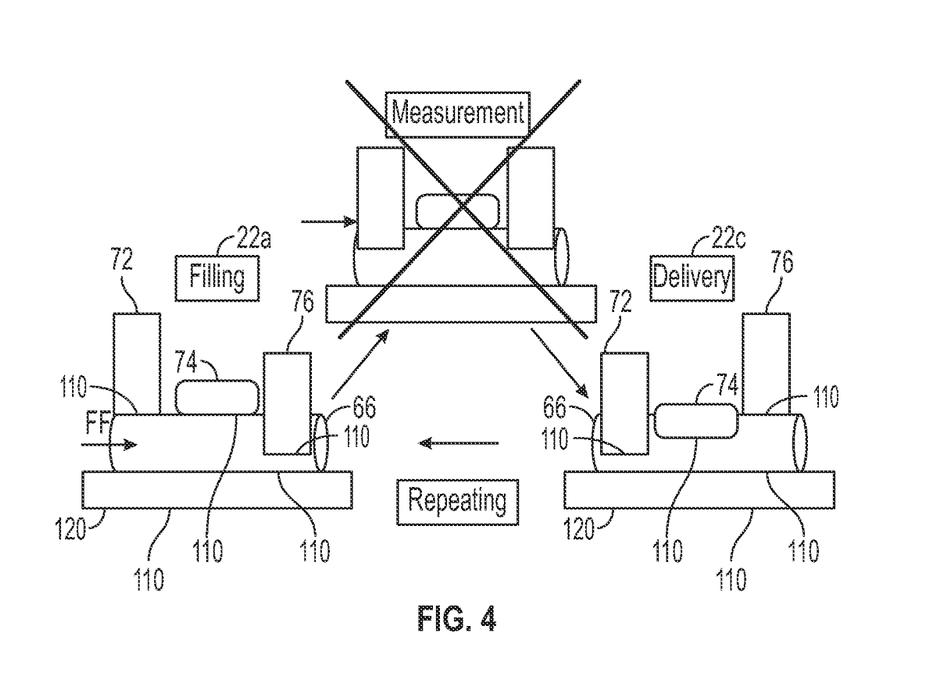
FIG. 4 depicts an illustration of another pump cycle of the infusion pump system of FIG. 2, according to aspects of the disclosure.

Turning now to FIG. 4, in some aspects of the disclosure an active infusion pump system 100 may eliminate the measurement phase 22b, and thus only require two sequential phases, the filling phase 22a and the delivery phase 22c.

Here, eliminating the volume measurement phase 22b is due to an improved flow delivery accuracy without the need of the feed-back loop mechanism design. Infusion pump system 100 includes binding contact interfaces 110 disposed between the tubing 66 and each of the upstream occluding finger 72, the primary pumping finger 74, the downstream occluding finger 76 and a backing surface 120 (e.g., the inner surface of door 50). The binding contact interfaces 110 couple the tubing 66 to each of the upstream occluding finger 72, the primary pumping finger 74, the downstream occluding finger 76 and the backing surface 120, causing the tubing 66 to move in concert with the connected surface. The binding contact interfaces 110 may keep the tubing 66 and the pump actuators 72, 74, 76 in contact at all times. Thus, tubing 66 compression and recovery, as well as open-close occlusion, may be fully controlled by the actuators 72, 74, 76 in real time. The resulting movement pattern of the tubing 66 along with the actuators 72, 74, 76 may cause the tubing 66 to avoid crashing during filling and may alleviate lateral friction-induced surface damage to the tubing 66.

In some aspects of the disclosure, any combination of the occluding finger 72, the primary pumping finger 74 and the downstream occluding finger 76 may have binding contact interfaces 110 connecting them to the tubing 66. For example, occluding fingers 72, 76 may not have binding contact interfaces 110 while the primary pumping finger 74 does.

As an example of function of the binding contact interfaces 110, during the medication delivery process 22c, when the upstream occluding finger 72 is lifted up to intentionally open the fluid path from a fully occluded position in the filling phase 22a, the tubing 66 is pulled up as well by being connected to the upstream occluding finger 72 via the binding contact interface 110 between them. Thus, the tubing 66 does not need to perform a mechanical resilience response in order to rebound quickly and attract enough fluid volume within a sub-second time scale. Similarly, the portions of the tubing 66 connected to each of the primary pumping finger 74 and the downstream occluding finger 76 via binding contact interfaces 110 will also be pulled up or out when the primary pumping finger 74 and the downstream occluding finger 76 pull up during the pump cycle. In addition, the binding contact interface 110 between the backing surface 120 and the tubing 66 keeps the tubing 66 from being pulled out of position (e.g., out of gap 54) in the pump system 100 by the pulling motion of any of the upstream occluding finger 72, the primary pumping finger 74 and the downstream occluding finger 76.

The binding contact interfaces 110 may be structured in various ways. According to some aspects of the disclosure, the tubing 66 may include a magnetic coating layer on the inner surface of the tubing 66 and/or the outer surface of the tubing 66. The upstream occluding finger 72, the primary pumping finger 74 and the downstream occluding finger 76 may be magnetic actuators. Thus, a magnetic attraction between the magnetic coating of the tubing 66 and the magnetic actuators 72, 74, 76 causes the tubing 66 to stick to and move in concert with the magnetic actuators 72, 74, 76.

In some aspects of the disclosure, magnetic material may be inserted into the walls of the tubing 66 instead having a magnetic coating on the tubing 66 surface(s). In some aspects of the disclosure, the material that forms the tubing 66 may include magnetic properties. For example, magnetic material may be introduced in the tubing 66 material as an additive during the extrusion process of forming the tubing 66 and then electrically magnetized.

In some aspects of the disclosure, magnetic material is formed on the tubing 66 (e.g., magnetic material coated on the surface, magnetic ink printed on the surface) or formed within the tubing material (e.g., magnets inserted into tubing walls, magnetic material extruded into the tubing material), and any or all of the upstream occluding finger 72, the primary pumping finger 74 and the downstream occluding finger 76 may be inductive magnetic actuators. Here, the inductive magnetic actuators may switch magnetic polarities, thus alternating between attracting and repelling the magnetic material in the tubing 66. Thus, the inductive magnetic actuators would not need to be physically attached to the tubing 66.

Figure 5:
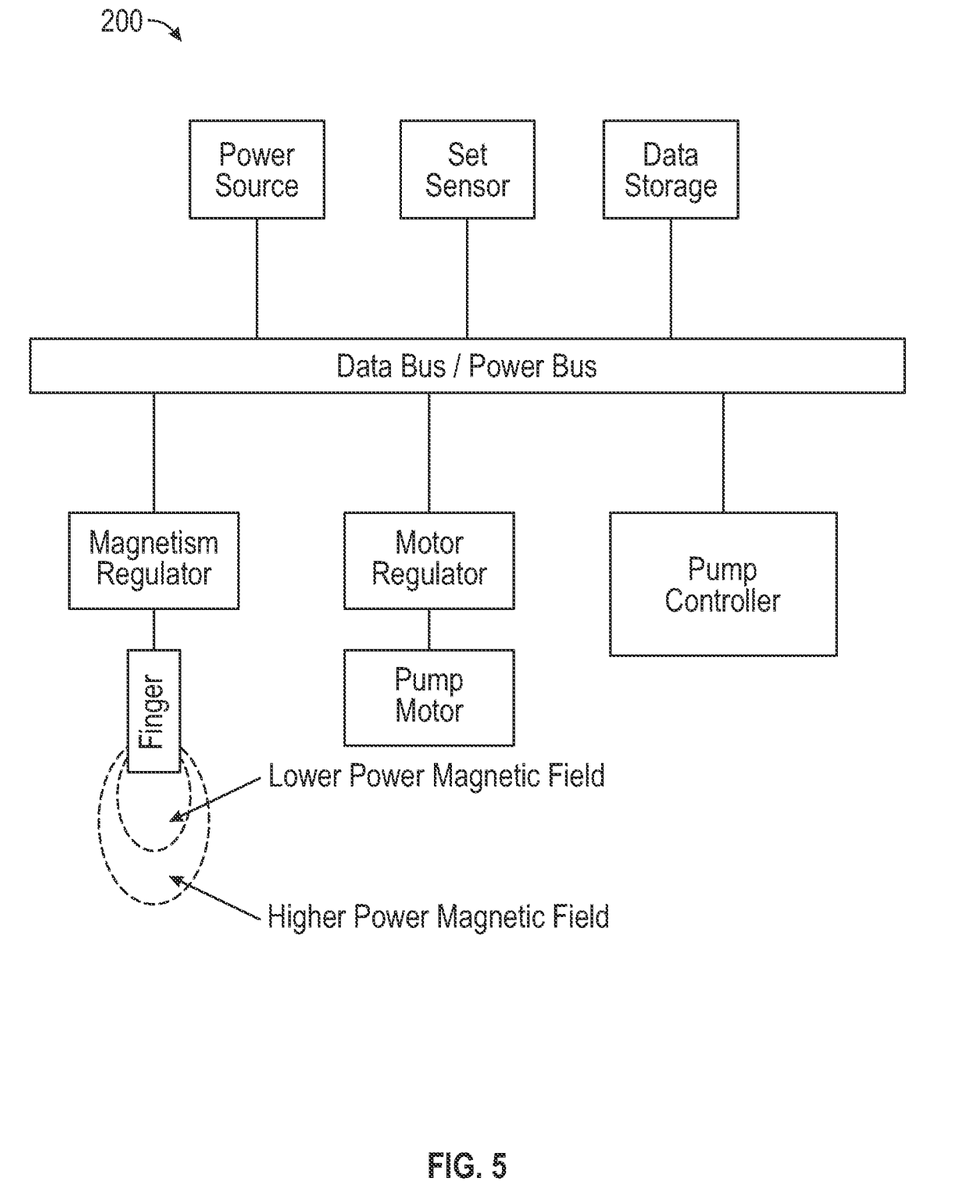
FIG. 5 depicts a schematic view of an infusion pump system, according to aspects of the disclosure.

As illustrated in the schematic layout of a pump 200 in FIG. 5, the activation of a pump finger (e.g., inductive magnetic actuator 72, 74, 76) may additionally or alternatively include adjusting the strength of the magnetic field generated based on, for example, the pumping set. For example, if the tubing (e.g., tubing 66) has a larger diameter the attractive surface may be closer to the pumping finger than tubing with a smaller diameter. In such instances, it may be desirable to conserve resources, such as power, needed to pump and activate the magnet to reduce abrasion as described. The amount of power provided to generate the inductive field may be reduced in such instances and increased to generate a larger field for smaller diameter tubing. As another example, different tubing 66 may include more or less magnetic material. In the case where the tubing includes more magnetic material, it may be desirable to conserve resources, such as power, needed to pump and activate the magnet to reduce the abrasion as described. Where the tubing has more magnetism or more magnetic material, it may require a smaller magnetic field than tubing with fewer magnetic properties. When the tubing is inserted into the pump (e.g., pump 22), identifying information may be detected by the pump. The pump may retrieve a configuration for the active magnetism from a data source accessible by the pump. The retrieval may be based on the identifying information such as by retrieving the configuration from a memory location using the identifying information. The pump controller (e.g., controller 60) may send control messages via a bus to a magnetism regulator and to a motor regulator. The magnetism regulator may cause a change in power (e.g., lower power magnetic field, higher power magnetic field) or a polarity of power (e.g., switch polarity) from the power source according to the control message.

Figure 6:
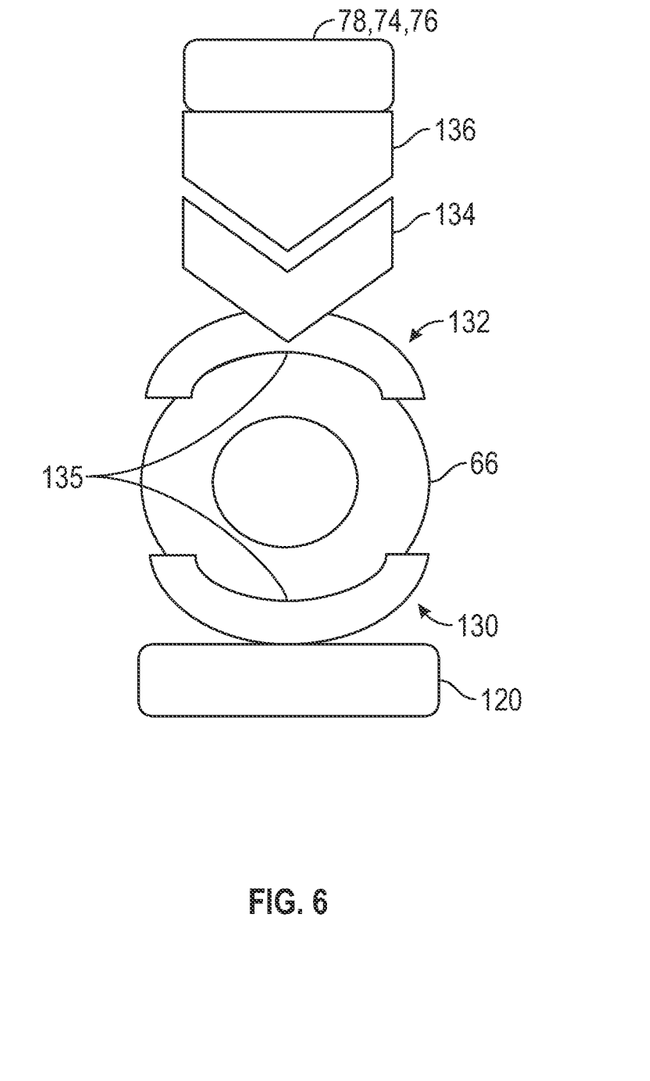
FIG. 6 depicts a cross-sectional side view of a binding interface assembly, according to aspects of the disclosure.

In some aspects of the disclosure, the binding contact interfaces 110 may include mechanical clamping with a pre-attached bracket on the tubing 66. For example, as shown in FIG. 6, a rigid tubing interface 130 (e.g., injection molded rigid plastic) may be bound to the tubing 66 with an adhesive 135 during intravenous (IV) set assembly and attached to the backing surface 120 to immobilize movement of the tubing 66 during pumping cycles. Similarly, a rigid tubing interface 132 having struts 134 may be bound to the tubing 66 with an adhesive 135. An actuator interface 136 may be attached to any of the upstream occluding finger 72, the primary pumping finger 74 and the downstream occluding finger 76, and linked to the struts 134. Both the connection between the tubing interface 130 and the backing surface 120, and the linkage between the struts 134 of tubing interface 132 and the actuator 72, 74, 76 may be easily attached and detached for the loading and unloading steps of the tubing 66 from the pump system 100.

In some aspects of the disclosure, any of the upstream occluding finger 72, the primary pumping finger 74, the downstream occluding finger 76 and the backing surface 120 may include a binding contact interface 110 configured as a suction device to provide vacuum suction on the tubing 66 surface. For example, the primary pumping finger 74 may be coupled to the tubing 66 via vacuum suction, where the primary pumping finger 74 pushes down on the tubing 66 during the delivery phase 22c, and pulls up on the tubing 66 during the filling phase 22a. The vacuum suction may be on during each pumping phase 22a, 22c, or the vacuum suction may only turn on during the filling phase 22a when the primary pumping finger 74 pulls away from the tubing 66 since the vacuum suction is not required for the primary pumping finger 74 to physically push down on the tubing 66 during the delivery phase 22c. For the backing surface 120, the vacuum suction may be turned on any of the entirety of the time the tubing 66 is loaded in the pump system 100, only when the pump system 100 is running and only when the actuator 72, 74, 76 is pulling away from the tubing 66.

In some aspects of the disclosure, the binding contact interface 110 may include a binding material (e.g., hook-and-loop patch such as a VELCRO™; adhesive patch) attached to the tubing 66 and a corresponding binding material attached to the actuator 72, 74, 76 or the backing surface 120. Here, the binding material may be attached to the tubing 66 with adhesive during the IV set assembly, and to any of the actuators 72, 74, 76 and the backing surface 120 any time prior to loading the tubing 66 into the pump system 100. Thus, when the tubing 66 is loaded into the pump system 100, the tubing 66 can be pressed down onto the backing surface 120 to engage the corresponding binding material of each surface. Further, when it is time to replace the tubing 66 or the IV set the tubing 66 is part of, the tubing 66 can simply be pulled free of the backing surface 120 and the actuators 72, 74, 76 and discarded.

In some aspects of the disclosure, the binding contact interfaces 110 may connect the actuators 72, 74, 76 to a fluid flow portion of a pump cassette instead of to the tubing 66. The pump cassette may already have a backing surface that holds the fluid flow portion in place. The binding contact interface 110 may connect any type of actuation device to a fluid flow portion of the cassette.

Figure 7:
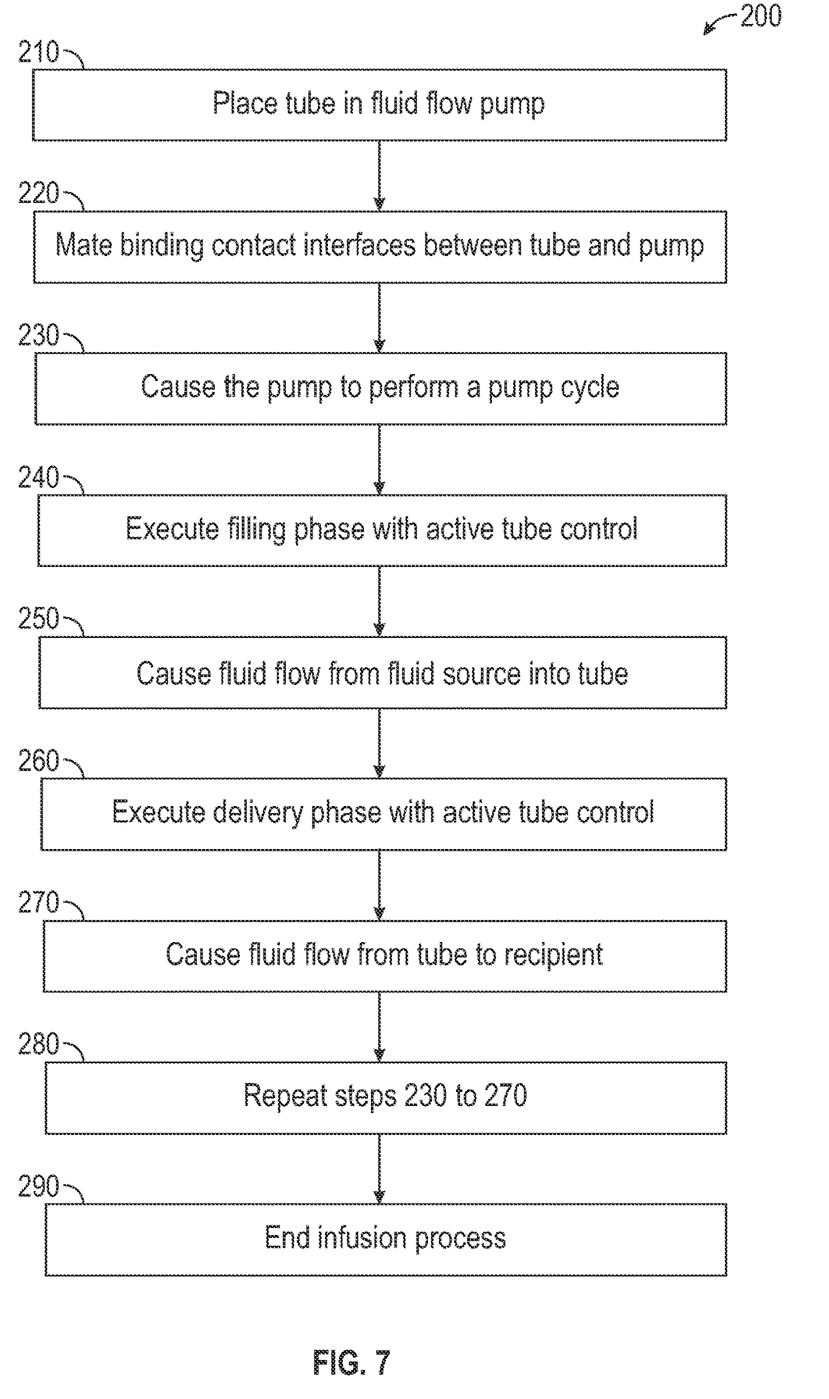
FIG. 7 illustrates a method of operating an infusion pump system, according to aspects of the disclosure.

According to some aspects of the disclosure, a method 200 of operating an infusion pump system is shown in FIG. 7. In step 210, an IV set tube (e.g., tubing 66) is placed or loaded into a fluid flow pump (e.g., pump system 100). Binding contact interfaces (e.g., binding contact interfaces 110) on the IV set tube are aligned and/or mated with binding contact interfaces (e.g., binding contact interfaces 110) on one or more actuators (e.g., upstream occluding finger 72, primary pumping finger 74, downstream occluding finger 76) and on an engagement surface (e.g., backing surface 120) opposing the actuators, in step 220. In step 230, the fluid flow pump is caused to perform a pump cycle.

In step 240, a fill portion of the pump cycle (e.g., filling phase 22a) is executed, causing a first actuator (e.g., upstream occluding finger 72) to move to or be positioned in a non-occluding position, causing a second actuator (e.g., downstream occluding finger 76) to move to or be positioned in an occluding position, and causing a third actuator (e.g., primary pumping finger 74) to move to or be positioned in a non-pumping position. Here, the binding contact interfaces between the IV set tube and the first and third actuators actively causes the IV set tube to fully open when the first and third actuators move in an outward direction from the IV set tube, without depending upon a passive resilience response of the IV set tube itself. Fluid flows from a fluid source (e.g., fluid supply 38) via an inlet tube (e.g., upstream fluid line 30) into the IV set tube (e.g., fluid flow FF) past the position of the first actuator and up to the occlusion in the IV set tube at the second actuator position, in step 250.

In step 260, a delivery portion of the pump cycle (e.g., delivery phase 22c) is executed, causing the first actuator to move to or be positioned in an occluding position, causing the second actuator to move to or be positioned in a non-occluding position, and causing the third actuator to move into a pumping position (e.g., press into the IV set tube). Again, the binding contact interface between the IV set tube and the second actuator actively causes the previously occluded IV set tube to fully open at the second actuator position when the second actuator moves in an outward direction from the IV set tube, without depending upon a passive resilience response of the IV set tube itself. Some or all of the fluid contained in the IV set tube between the first and second actuators flows downstream from the second actuator position into an outlet tube (e.g., downstream fluid line 31) and to a fluid recipient (e.g., patient 48), in step 270. In step 280, the system returns to step 230 to execute another pump cycle. The method ends in step 290 when the infusion is finished or the pump is stopped.

As used herein, the terms "control" or "controlling" encompass a wide variety of actions. For example, "controlling" a device may include transmitting one or more messages to adjust an operational state or functional element of the device. The message may include specific instructions to be executed by a processor of the device to manifest the change. The "controlling" may include storing a value in a location of a storage device for subsequent retrieval by the device to be controlled, transmitting a value directly to the device to be controlled via at least one wired or wireless communication medium, transmitting or storing a reference to a value, and the like. For example, a control message may include a value to adjust a level of power from a power source of the controlled device. As another example, a control message may activate or deactivate a structural element of the controlled device such as a light, audio playback, a motor, a lock, a pump, a display, or other component of a device described herein. "Controlling" may include indirect control of the device by adjusting a configuration value used by the controlled device. For example, the control message may include a threshold value for a device characteristic (e.g., temperature, rate, frequency, etc.). The threshold value may be stored in a memory location and referred to by the controlled device during operation.

According to some aspects of the disclosure, a pump assembly includes a fluid flow pump, a tubing pathway configured to receive a fluid tube and a tubing dimension measurement assembly. The tubing dimension measurement assembly includes a processor, an emitter spaced from the tubing pathway and configured to generate an emission into the tubing pathway, and a collector spaced from the tubing pathway, the collector disposed to receive the emission from the emitter, wherein the tubing dimension measurement assembly is further configured to measure an outer diameter (OD) of a tube received in the pathway, wherein said measurement is based at least in part on the emission.

It is understood that any specific order or hierarchy of blocks in the methods of processes disclosed is an illustration of example approaches. Based upon design or implementation preferences, it is understood that the specific order or hierarchy of blocks in the processes may be rearranged, or that all illustrated blocks be performed. In some implementations, any of the blocks may be performed simultaneously.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

As used herein, the terms "determine" or "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, inserting and the like via a hardware element.

As used herein, the term "message" encompasses a wide variety of formats for communicating (e.g., transmitting or receiving) information. A message may include a machine readable aggregation of information such as an XML document, fixed field message, comma separated message, or the like. A message may, in some implementations, include a signal utilized to transmit one or more representations of the information. While recited in the singular, it will be understood that a message may be composed, transmitted, stored, received, etc. in multiple parts.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

In any embodiment, data can be forwarded to a "remote" device or ocation," where "remote," means a location or device other than the location or device at which the program is executed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the interne or including email transmissions and information recorded on websites and the like.

Some embodiments include implementation on a single computer, or across a network of computers, or across networks of networks of computers, for example, across a network cloud, across a local area network, on hand-held computer devices, etc. The computers may be physical machines or virtual machines hosted by other computers. In certain embodiments, one or more of the steps described herein are implemented on a computer program(s). Such computer programs execute one or more of the steps described herein. In some embodiments, implementations of the subject method include various data structures, categories, and modifiers described herein, encoded on computer-readable medium(s) and transmissible over communications network(s).

Software, web, internet, cloud, or other storage and computer network implementations of the present invention could be accomplished with standardized programming techniques specifically adapted to cause one or more device to perform the various assigning, calculating, identifying, scoring, accessing, generating or discarding steps described.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A medical pumping system, comprising:
   a fluid pump comprising:
      a fluid inlet connection;
      a fluid outlet connection;
      an actuator; and
      a backing surface;

a tube of an intravenous set disposed between the fluid inlet connection and the fluid outlet connection of the fluid pump, and disposed between the actuator and the backing surface; and a binding contact interface disposed between the tube and the actuator, the binding contact interface comprising a tubing interface coupled to the tube; and an actuator interface coupled to the actuator, wherein the tubing interface comprises a strut sized and shaped to link to the actuator interface, the strut disposed between the tube and the actuator interface, wherein the tube and the actuator are coupled together by the binding contact interface, and wherein the actuator is configured to actively pull a portion of the tube into an open position during a pump cycle.

2. The medical pumping system of claim 1, wherein the tubing interface comprises an arced portion coupled to the tube by an adhesive, and wherein each of the actuator interface and the strut are v shaped.

3. The medical pumping system of claim 1, further comprising:

an additional binding contact interface, wherein the tube and the backing surface are coupled together by the additional binding contact interface, the additional binding contact interface configured to prevent the tube from pulling away from the backing surface.

4. The medical pumping system of claim 3, wherein the additional binding contact interface comprises:

a hook-and-loop patch coupled to the backing surface; and a hook-and-loop patch coupled to the tube.

5. The medical pumping system of claim 3, wherein the additional binding contact interface comprises:

an adhesive patch coupled to the backing surface; and
an adhesive patch coupled to the tube.

6. The medical pumping system of claim 3, wherein the additional binding contact interface comprises:

at least a portion of the backing surface comprising a vacuum interface, wherein the backing surface is coupled to the tube by vacuum suction.

7. The medical pumping system of claim 1, further comprising:

wherein the actuator is a plurality of actuators, comprising:
an upstream occluding finger;
a downstream occluding finger; and
a primary pumping finger; and first, second and third binding contact interfaces, wherein the first binding contact interface couples the upstream occluding finger to a first portion of the tube, the second binding contact interface couples the downstream occluding finger to a second portion of the tube, and the third binding contact interface couples the primary pumping finger to a third portion of the tube.

8. A medical pumping system, comprising:
a fluid pump comprising:
a fluid inlet connection;
a fluid outlet connection;
an actuator; and
a backing surface;

a tube of an intravenous set disposed between the fluid inlet connection and the fluid outlet connection of the fluid pump, and disposed between the actuator and the backing surface; and a binding contact interface, wherein the binding contact interface comprises:

at least a portion of the actuator comprising a magnetic inductor; and at least a portion of the tube is magnetic, wherein the actuator is configured to switch magnetic polarities to alternately attract and repel the magnetic tube portion, wherein the tube and the actuator are coupled together by the binding contact interface, and wherein the actuator is configured to actively pull a portion of the tube into an open position during a pump cycle.

9. The medical pumping system of claim 8, further comprising:

an additional binding contact interface, wherein the tube and the backing surface are coupled together by the additional binding contact interface, the additional binding contact interface configured to prevent the tube from pulling away from the backing surface.

10. The medical pumping system of claim 9, wherein the additional binding contact interface comprises:

a hook-and-loop patch coupled to the backing surface; and a hook-and-loop patch coupled to the tube.

11. The medical pumping system of claim 9, wherein the additional binding contact interface comprises:

an adhesive patch coupled to the backing surface; and
an adhesive patch coupled to the tube.

12. The medical pumping system of claim 9, wherein the additional binding contact interface comprises:

at least a portion of the backing surface comprising a vacuum interface, wherein the backing surface is coupled to the tube by vacuum suction.

13. The medical pumping system of claim 8, further comprising:

wherein the actuator is a plurality of actuators, comprising:
an upstream occluding finger;
a downstream occluding finger; and
a primary pumping finger; and first, second and third binding contact interfaces, wherein the first binding contact interface couples the upstream occluding finger to a first portion of the tube, the second binding contact interface couples the downstream occluding finger to a second portion of the tube, and the third binding contact interface couples the primary pumping finger to a third portion of the tube.

14. A medical pump, comprising:
a fluid inlet connection;
a fluid outlet connection;
an actuator configured to compress a portion of an intravenous tube, wherein one of:
the actuator is coupled to a first binding contact interface; and
the actuator comprises a first binding contact interface;

a backing surface opposing the actuator, wherein one of:
the backing surface is coupled to a second binding contact interface; and
the backing surface comprises a second binding contact interface, wherein the first and second binding contact interfaces are configured to couple with first and second portions of the tube, respectively;

an actuator interface coupled to the actuator; and a tubing interface configured to be coupled to the tube, the tubing interface comprising a strut sized and shaped to link to the actuator interface, the strut disposed between the tube and the actuator interface, wherein the actuator is configured to actively pull a portion of the tube into an open position during a pump cycle via the coupling of the first binding contact interface to the first portion of the tube, and wherein the backing surface is configured to hold the tube in place during the pump cycle via the coupling of the second binding contact interface to the second portion of the tube.

15. The medical pump of claim 14, wherein the second binding contact interface comprises one of a hook-and-loop patch, an adhesive patch, a rigid actuator interface, a magnet, an inductor and a vacuum source.

16. The medical pump of claim 15, further comprising:
wherein the actuator is a plurality of actuators, comprising:
- an upstream occluding finger;
- a downstream occluding finger; and
- a primary pumping finger, wherein the first binding contact interface couples the upstream occluding finger to the first portion of the tube, a third binding contact interface couples the downstream occluding finger to a third portion of the tube, and a fourth binding contact interface couples the primary pumping finger to a fourth portion of the tube.

* * * * *

UNITED STATES PATENT AND TRADEMARK OFFICE
CERTIFICATE OF CORRECTION

| | | |
|---|---|---|
| PATENT NO. | : 12,029,879 B2 | Page 1 of 1 |
| APPLICATION NO. | : 17/379692 | |
| DATED | : July 9, 2024 | |
| INVENTOR(S) | : Fanqing Meng et al. | |

It is certified that error appears in the above-identified patent and that said Letters Patent is hereby corrected as shown below:

In the Claims

Column 15, Line 13 (Claim 16): Replace "The medical pump of claim 15," with --The medical pump of claim 14--.

Signed and Sealed this
Thirteenth Day of August, 2024

Katherine Kelly Vidal
*Director of the United States Patent and Trademark Office*